(12) United States Patent
Cho et al.

(10) Patent No.: US 11,880,855 B2
(45) Date of Patent: Jan. 23, 2024

(54) BLOCK CHAIN-BASED HEALTH DATA MANAGEMENT SYSTEM AND DRIVING METHOD OF SAME

(71) Applicant: CLINOMICS INC., Ulsan (KR)

(72) Inventors: Su An Cho, Hwaseong-si (KR); Jong Hwa Bhak, Ulsan (KR)

(*) Notice: Subject to any disclaimer, the term of this patent is extended or adjusted under 35 U.S.C. 154(b) by 0 days.

(21) Appl. No.: 17/621,505

(22) PCT Filed: Aug. 20, 2019

(86) PCT No.: PCT/KR2019/010565
§ 371 (c)(1),
(2) Date: Dec. 21, 2021

(87) PCT Pub. No.: WO2021/025222
PCT Pub. Date: Feb. 11, 2021

(65) Prior Publication Data
US 2022/0366442 A1    Nov. 17, 2022

(30) Foreign Application Priority Data

Aug. 2, 2019   (KR) .................. 10-2019-0094420

(51) Int. Cl.
G06Q 30/00       (2023.01)
G06Q 30/0208    (2023.01)
G16H 10/60      (2018.01)

(52) U.S. Cl.
CPC ......... *G06Q 30/0208* (2013.01); *G16H 10/60* (2018.01)

(58) Field of Classification Search
CPC .................................................. G16H 10/60
See application file for complete search history.

(56) References Cited

U.S. PATENT DOCUMENTS

| | | | |
|---|---|---|---|
| 2019/0355472 A1* | 11/2019 | Kutzko | G16H 20/10 |
| 2019/0392928 A1 | 12/2019 | Hosseini et al. | |
| 2020/0388365 A1* | 12/2020 | Ponceleon | G16H 50/20 |

FOREIGN PATENT DOCUMENTS

| | | | |
|---|---|---|---|
| KR | 10-0425370 | 3/2004 | |
| KR | 10-2005-0051785 | 6/2005 | |
| KR | 10-2009-0014781 | 2/2009 | |
| KR | 10-1132431 | 3/2012 | |
| KR | 10-1881045 | 7/2018 | |
| KR | 10-1946555 | 5/2019 | |
| KR | 2020025756 A * | 3/2020 | G16H 10/60 |

OTHER PUBLICATIONS

English Specification of 10-1946555.
English Specification of 10-1881045.
English Specification of 10-1132431.
Jul. 11, 2018, LG Blog Management Attractive Technology to Change the World-Blockchain, and Monachain. LG Official blog.
Jan. 2018, No. 79, pp. 1-19, Kang, Min Yeong et al. The Present and Future of Smart Healthcare. Issue Monitor. Samjong KPMG ERI.
English translation of "Jul. 11, 2018, LG Blog Management Attractive Technology to Change the World-Blockchain, and Monachain. LG Official blog."
English translation of "Jan. 2018, No. 79, pp. 1-19, Kang, Min Yeong et al. The Present and Future of Smart Healthcare. Issue Monitor. Samjong KPMG ERI".
English Specification of 10-2009-0014781.
English Specification of 10-0425370.
English Specification of 10-2005-0051785.
Grishin Oennis et al: "Accelerating Genomic Oata Generation and Facilitating Genomic Oata Access Using Oecentralization, Privacy-Preserving Technologies and Equitable Compensation", Blockchain in Heal thcare Tooay vol. 1, Dec. 17, 2018 (Dec. 17, 2018), pp. 1-23.
Allison Ackerman Shrier et al: "Blockchain and health IT: Algorithms, Privacy, and Oata—Whitepaper", US Fed News Service, Including US State News, Aug. 30, 2016 (Aug. 30, 2016), XP055569588, Washington O.C.
Nikolay Kulemin et al: "The Zenome Project: Whitepaper blockchainbased genomic ecosystem", Sep. 21, 2017 (Sep. 21, 2017), XP055736413, 001: 10.13140/rg.2.2.25865.13925.

* cited by examiner

*Primary Examiner* — Alvin L Brown
(74) *Attorney, Agent, or Firm* — ANTONIO HA & U.S. PATENT, LLC

(57) ABSTRACT

The present invention relates to a driving method of a block chain-based health data management system. When personal health data such as health examination or prescription data and the like is uploaded, a genome portal: stores the personal health data as metadata together with genetic information; provides the personal health data so that a demand agency requiring the personal health data can use Zerocoin to purchase or read the personal health data through the genome portal; provides rewards in the form of mileage to individuals who share the data in the genome portal; ranks the individuals by the number of times the individuals have shared the data; automatically presents various personalized health solutions in the portal through AI according to the shared data; provides a rapidly growing personal genome prediction/diagnosis service through a portal system by using a blockchain-based MS decentralized identity (DID) in order to enhance the security of the email addresses and IDs of users; and ascribes value to personal health big data, such as genome data, medical diagnosis information, or social data, and so as to reduce the costs of personal genetic testing and diagnosis.

10 Claims, 4 Drawing Sheets

BLOCK CHAIN-BASED HEALTH DATA MANAGEMENT SYSTEM AND DRIVING METHOD OF SAME

TECHNICAL FIELD

The present invention relates to a method of driving a blockchain-based health data managing system and, in particular, to a method of driving a blockchain-based health data managing system to manage personal health data, such as genetic information, checkups, or prescriptions.

BACKGROUND ART

Global medical markets are facing a drastic change with technical growth of diagnosis industry.

In particular, significantly lowered genetic testing costs are quickly expanding personal genetic analysis service markets. As mutant genes and epigenetic variations which have not been known thus far are studied and revealed, diagnosis and research and development for new medicines are underway by single nucleotide polymorphism (SNP) and epigenetic bio-markers.

Personal genome testing markets are on the rise. Specifically, global DTC markets, which amounted to 600 million dollars in year 2017, will see 2.5 billion dollars in year 2024. The U.S. market was assessed to have about 8 million DTC testing cases in year 2018 and the market size is forecast to reach about 500 to 600 million dollars.

Further, the market for early cancer diagnosis through liquid biopsy is taking place. Specifically, the global liquid biopsy market is expected to grow from $700 million in 2017 to $1.2 billion in 2022, i.e., a CAGR+14%. Development of companion diagnostic products for customized prescription is expanding as well. The global diagnosis market is expected to grow from $3.2 billion in 2017 to $5.7 billion in 2022, i.e., CAGR+13%.

Meanwhile, blockchain technology has been developed to block off hacking in online financial transactions.

The blockchain is also known to allow for secure transactions on bitcoin which is a sort of cryptocurrency. Blockchain technology, as patent-free open source software, is being rapidly adopted by worldwide financial companies which have realized its value. Use of such technology may save massive costs which may be consumed for maintenance and security of customer ledgers (DB).

In other words, conventional financial companies have retained transaction records in their centralized server. By blockchain technology, however, transaction information is saved in network participants' computers, and any additional transaction requires authorization by all the participants.

Blockchain ledgers are fully opened online, and while encoding and decoding are repeated, cross-checks are conducted every certain period of time for verification purposes, so that hacking may be fundamentally blocked off.

Further, blockchain technology, by its decentralized nature, enables transactions without involvement of a bank or other organizations. All participants are allowed to see all transactions, which ensures transaction transparency, and transaction information, once recorded, cannot be altered or deleted.

Current Internet technology is useful for neutral information sharing. However, there is a big limitation in sharing information that contains value. In practice, identity (ID) information may be regarded as most critical value-containing information.

Over the Internet, a person's ID information may be indefinitely copied and used by others. A copy of a financial account may arbitrarily control its original and allow for use of public services. To prevent such circumstance and share ID information, the conventional Internet environment requires a certificate ensured by a reliable third party.

However, obtaining and using such a certificate is burdensome and inconvenient and, despite use of a certificate, the likelihood of ID data leakage and theft still remains.

In contrast, dAPPs adopted by blockchain technology support IDs and address the forgoing issues. For example, dAPPs may prevent distortion of personal information and authenticate IDs even without entrusting all personal information to the user, thereby freeing them of the information leakage issue. Further, one may possess the authority to control her own ID information.

In the Internet environment, ID authentication is a must to apps needing purchasing power or to receive financial or governmental services. Conventional ID authentication is slow, has the risk of ID leakage, and is inefficient. However, use of decentralized IDs (DIDs) enables opening a new bank account within just a few seconds, subscription to Facebook, and receiving government services. This may lead to savings in time, efforts, and costs. Thus, DIDs are forecast to have more demand.

With early disease diagnosis markets flowering, there will be introduced prescription and life services which are customized for ones' individual genome features. Thus, a need arises for a system for providing a genetic information web portal, and payment and compensation services.

DETAILED DESCRIPTION OF THE INVENTION

Technical Problems

The present invention has been conceived based on the foregoing technical background and aims to provide a health data managing service providing system and method of driving the same, which may make personal health bigdata value and relieve persons of genetic testing and medical costs.

Another object of the present invention is to provide a health data managing service providing system and method of driving the same, which may provide a customized healthcare solution to each person.

Means to Address the Problems

To achieve the above objectives, the present invention includes the following components.

According to an embodiment, a blockchain-based health data managing system comprises an information managing unit configured to receive user health data including at least one of genetic information, checkup information, and prescription information from a user terminal, store the user health data, and manage user information and the user health data in a blockchain-based decentralized identity (DID) manner, an information providing unit configured to, upon receiving a request for user health data from a health data demanding organization, extract part of the user health data managed by the information providing unit and provide the extracted information, and a payment processing unit configured to receive a cryptocurrency as a return on providing the user health data from the health data demanding organization and provide a cryptocurrency as a reward for providing the user health data to a user who has provided the user health data.

According to an embodiment, a method of driving a blockchain-based health data managing system comprises a step in which an information managing unit receives user health data including at least one of genetic information, checkup information, and prescription information from a user terminal, stores the user health data, and manages user information and the user health data in a blockchain-based decentralized identity (DID) manner, a step in which an information providing unit, upon receiving a request for user health data from a health data demanding organization, extracts part of the user health data managed by the information providing unit and provides the extracted information; and a step in which a payment processing unit receives a cryptocurrency as a return on providing the user health data from the health data demanding organization and provides a cryptocurrency as a reward for providing the user health data to a user who has provided the user health data.

Effects of the Invention

The present invention may provide personal genome prediction/diagnosis services, which are drastically growing, via a web portal system and make profits personal health bigdata, e.g., genome, medical diagnosis, or social data information, thereby relieving users of genetic test costs and diagnosis costs.

In particular, rewarding may be performed with a dedicated blockchain cryptocurrency, e.g., Zerocoin, without any hassles or inconvenience which would otherwise arise when certificates are used for authentication. Further, the present invention may prevent the risk of ID data leakage or theft.

Further, the present invention may establish a health data management web portal service platform capable of providing individual customized health solutions.

BEST MODE TO PRACTICE THE INVENTION

The terms as used herein are provided merely to describe some embodiments thereof, but not to limit the present disclosure. The terms as used herein are provided merely to describe some embodiments thereof, but not to limit the scope of other embodiments of the present disclosure. Unless otherwise defined, all terms including technical and scientific terms used herein have the same meaning as commonly understood by one of ordinary skill in the art to which the embodiments of the present invention pertain and should not be interpreted as overly broad or narrow.

Hereinafter, preferred embodiments of the present invention are described in detail with reference to the accompanying drawings.

Figure 1:
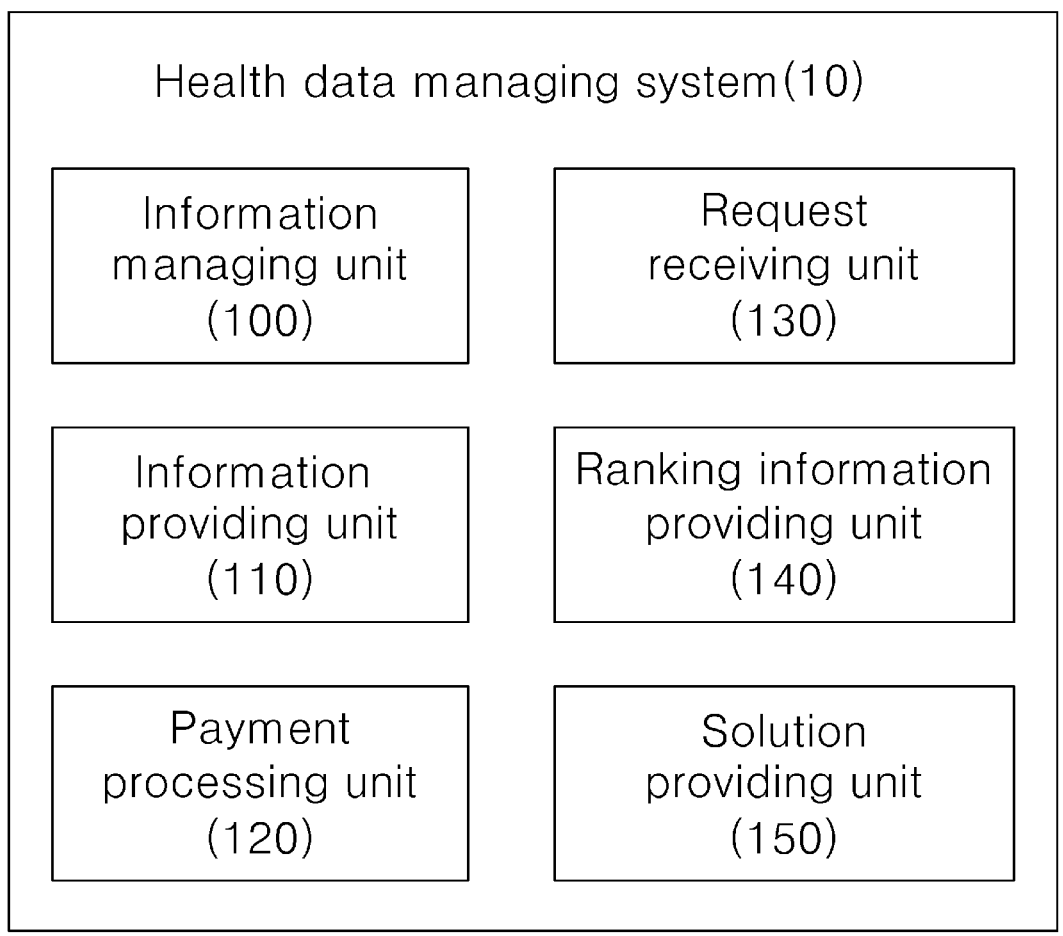
FIG. 1 is a block diagram illustrating a configuration of a health data managing system according to an embodiment of the present invention.

FIG. 1 is a block diagram illustrating a configuration of a health data managing system according to an embodiment of the present invention.

According to an embodiment of the present invention, a user uploads her own health bigdata onto a health data managing system. The health data managing system provides cryptocoins, such as Zerocoin, to the user as a reward. In other words, the user may make her health bigdata value and obtain cryptocoins, such as Zerocoin.

The health bigdata may include genome information, i.e., genetic information, medical information, or social data.

According to an embodiment, the health data managing system may create the user's health data into metadata and store the metadata on a blockchain basis.

The user may get genetic testing to obtain her genetic information (DNA, RNA, epigenetic variations, gene mutants, gene group, and all genomes). Genotyping may be performed and gene-associated information may be stored and managed by a method of uploading resultant data of tests already performed.

According to an embodiment, the health data managing system may create the user's health data into bigdata and stably store the health data as bigdata. The health data managing system may provide the stored health data, i.e., bigdata, to organizations which demand the health data when they pay for or are allowed to view it. The demanding organizations may include pharmaceutical companies, medical device manufacturers, insurance companies, food/cosmetics companies, research institutes, schools, or bio companies. However, embodiments of the disclosure are not limited thereto.

The health data managing system may recommend a solution optimized for the user based on the bigdata including the health data. The solution may include information about health supplement foods, cosmetics, customized supplements or medications, and medical organizations. However, without limitations, the solution may include other various pieces or types of information necessary for healthcare. The health data managing system may provide a user interface which may not simply provide information but also lead to purchase of goods in association with local shopping malls.

According to an embodiment, the health data managing system may provide various types of health-related services including genetic testing and thereby create profits. The health data managing system may also provide a business model that may realize health bigdata banking and transaction fees by selling and brokering personal health bigdata.

Further, the health data managing system may propose business models, which may make profits via advertisements, to individuals or health data demanding organizations, such as pharmaceutical companies, medical device manufacturers, insurance companies, food/cosmetics companies, research institutes, schools, or bio companies.

The health data demanding organizations may add online advertisements to the genome web portal in which case advertisement fees may be paid only via Zerocoins. As such, there may be proposed a business model which may make profits via advertisements.

Further, according to an embodiment, the health data managing system may provide personal gene prediction, diagnosis services which are now growing drastically. To relieve ones of their genetic testing or diagnosis costs, rewarding via cryptocurrency which the health data managing system issues on its own may be performed.

Referring to FIG. 1, according to an embodiment, the health data managing system includes an information managing unit 100, an information providing unit 110, a payment processing unit 120, a request receiving unit 130, a ranking information providing unit 140, and a solution providing unit 150.

The information managing unit 100 receives user health data including at least one of genetic information, checkups, or prescriptions from a user terminal, stores and manages the user health data. The information managing unit 100 manages user information and the user health data in a blockchain-based decentralized identity (DID) manner (e.g., MS decentralized identity (DID)).

The decentralized identity (DID) is blockchain-based electronic identity verification technology that stores users' personal information in the users' terminal, i.e., user terminals and, upon authentication, allows only information necessary for authentication to be selected and provided.

Most of businesses and organizations store and manage personal information in their central systems. However, the DID allows individuals to manage their personal information on their own.

Centralized systems may have the risk of leakage of massive personal information when hacking occurs and may be vulnerable to embezzlement or appropriation of personal information by companies.

However, the DID allows individual users themselves to manage their personal information and distributes and stores the information in the individual users' user terminals. Use of the DID eliminates the need for providing all personal information upon performing authentication for use of services and rather selects and provides only necessary information.

The DID, also called a self-sovereign identity, may call in only prior authentication information without the need for login or authentication at each time it is required. Thus, the DID may relieving users of such hassles or inconveniences as photographing, scanning or copying their ID card or entering information whenever required.

The user's gene (genome) data is uploaded once by the information managing unit 100, but medical information, such as checkup results or prescriptions, or social data is continuously uploaded and accrued over time, Thus, the information managing unit 100 preferably steadily uploads individuals' health data so that such information or data may have continuity.

Upon receiving a request for user health data from a health data demanding organization, the information providing unit 110 extracts part of the user health data managed by the information managing unit 100 and provides the extracted information.

The health data demanding organization may be one of pharmaceutical companies, medical device manufacturers, insurance companies, food/cosmetics companies, research institutes, or schools. Without limitations, however, the health data demanding organization is interpreted to encompass all other kinds or types of business, enterprises, organizations or groups which need users' health-related information.

According to an embodiment, the health data managing system 10 adopts the blockchain-based DID (e.g., MS DID) to reinforce the security of users' personal email addresses and IDs.

According to an embodiment, while the user's health bigdata is shared, the data owner may be anonymously handled, and the network address of the genome web portal provided by the health data managing system 10 is treated as an encryption identity which is unrelated to the personal information.

Thus, purchases of health data are limited to transparent persons whose identities have been verified by the health data managing system 10, and all transaction records are perpetually stored in the genome web portal blockchains the health data managing system 10 provides.

The request for user health data from the health data demanding organization may include filtering reference information about the health data. For example, the filtering reference information may include filtering references, such as the user's gender and age and whether they suffer from a particular disease. The information providing unit 110 extracts and provides user health data that meets the filtering references included in the user health data request received from the health data demanding organization.

Thus, the health data managing system 10 may provide a genetic information providing-customized search engine weighted depending on the user's health and genetic information.

The payment processing unit 120 receives a cryptocurrency, as a return on providing the user health data, from the health data demanding organization and provide the user, who has provided the user health data, with a cryptocurrency as a reward for providing the user health data.

Members who provide or share their personal checkup information, e.g., health data, may be exempt from or be given a discounted rate for genetic testing costs.

In an embodiment, the cryptocurrency may be a self-issued virtual currency. Self-issued virtual currency, that is, Zerocoin, calculates the value of 1 coin as a unit of human lifespan. Any time unit, such as hour, second, minute, or day, may belong to the concept of Zerocoin. The concept of Zerocoin is to translate any goods, services, or capital, which may lengthen or lessen human life, into coins.

As an example, in the hypothesis that a person lives 100 years, i.e., 36,500 days, one day may correspond to one Zerocoin, and 292,000,000,000,000 Zerocoins, which results from multiplying the current total global population, i.e., 8,000,000,000 by 36,000 days, may be issued.

Zerocoin is not limited to particular coinage systems but may be applied to systems that the applicant develops and builds up. Further, a dedicated local exchange may be developed and established in which Zerocoin transactions may be made.

The payment processing unit 120 may interact with a Zerocoin payment system (Genopay) which may be used in a local shopping mall associated with the health data managing system 10. The local shopping mall may take cash, credit cards, or Zerocoin as payment means. However, embodiments of the disclosure are not limited thereto.

According to an embodiment, the health data managing system 10 may identify various genetic testing reports on web and mobile via bar-code authentication. The health data managing system 10 has a Genopay function that enables payment for a genetic testing service using cryptocurrency. Further, the health data managing system 10 function as a local virtual currency exchange where only Zerocoin may be transacted. The health data managing system 10 may provide a mobile app functions for Zerocoin transactions by individuals or in hospitals/checkup centers or health data demanding organizations.

According to an embodiment, the health data managing system 10 may further include the request receiving unit 130. The request receiving unit 130 receives a request for genetic testing or a checkup request from the user terminal.

The user may access the genome web portal, which the health data managing system 10 provides, by way of the user terminal to thereby request a genetic testing service and conduct a survey. The request receiving unit 130 provides various surveys (for, e.g., personalities, propensities, characters, health, or aptitude) to gather personal social data.

The request receiving unit 130 may recommend a test organization or book a test for the user's genetic testing based on the genetic testing service request and the results of the survey.

The information managing unit 100 obtains the results of the genetic test performed according to the genetic test request and stores and manages the results as user health data. The information managing unit 100 may obtain the genetic test results from the user terminal or directly from the test organization which was recommended or booked for.

The payment processing unit 120 receives a cryptocurrency as a return on the checkup request or genetic test request received from the user terminal by the request receiving unit 130. The payment processing unit 120 deducts a predetermined rate of handling fees from the return on the genetic test request or checkup request and provides the resultant money to the genetic test organization or checkup organization. The money provided to the genetic test organization or checkup organization may be preferably in the form of cryptocurrency.

According to an embodiment of the present invention, the health data managing system 10 further includes the ranking information providing unit 140. The ranking information providing unit 140 counts the number of times in which the information providing unit 110 provides user health data in response to requests from the health data demanding organization and provides data providing ranking information.

In other words, the ranking information providing unit 140 counts the numbers of times in which user health data has been provided to pharmaceutical companies, medical device manufacturers, insurance companies, food/cosmetics companies, research institutes, schools, or other health data demanding organizations and rank them in descending order of the numbers of times. The ranking information is provided to the users who uploaded their health data or to the health data demanding organizations.

According to an embodiment of the present invention, the health data managing system 10 further includes the solution providing unit 150.

The solution providing unit 150 determines health supplement foods, customized medication, or customized medical organization information, which is necessary to the user, based on artificial intelligence (AI) and the user health data and provides an individual customized health solution. The health solution is interpreted to encompass all kinds or pieces of information which may contribute to the user's health, such as exercise information or diet information helpful for staying healthy or cosmetics.

The solution providing unit 150 may also recommend the user for the optimized solution (e.g., health supplement food, cosmetics, customized medication, or customized medical organization information) based on personal health, gene, or social information and allow the user to purchase relevant products in the shopping malls in the web portal operated by the health data managing system 10.

According to an embodiment, the health data managing system 10 may assign weights to health bigdata and score each piece of user health data reflecting a data value. For example, the health data managing system 10 may assign a higher weight to health data of a specific genetic structure or diathesis and differentially request or reward coins for sharing such data.

Figure 2:
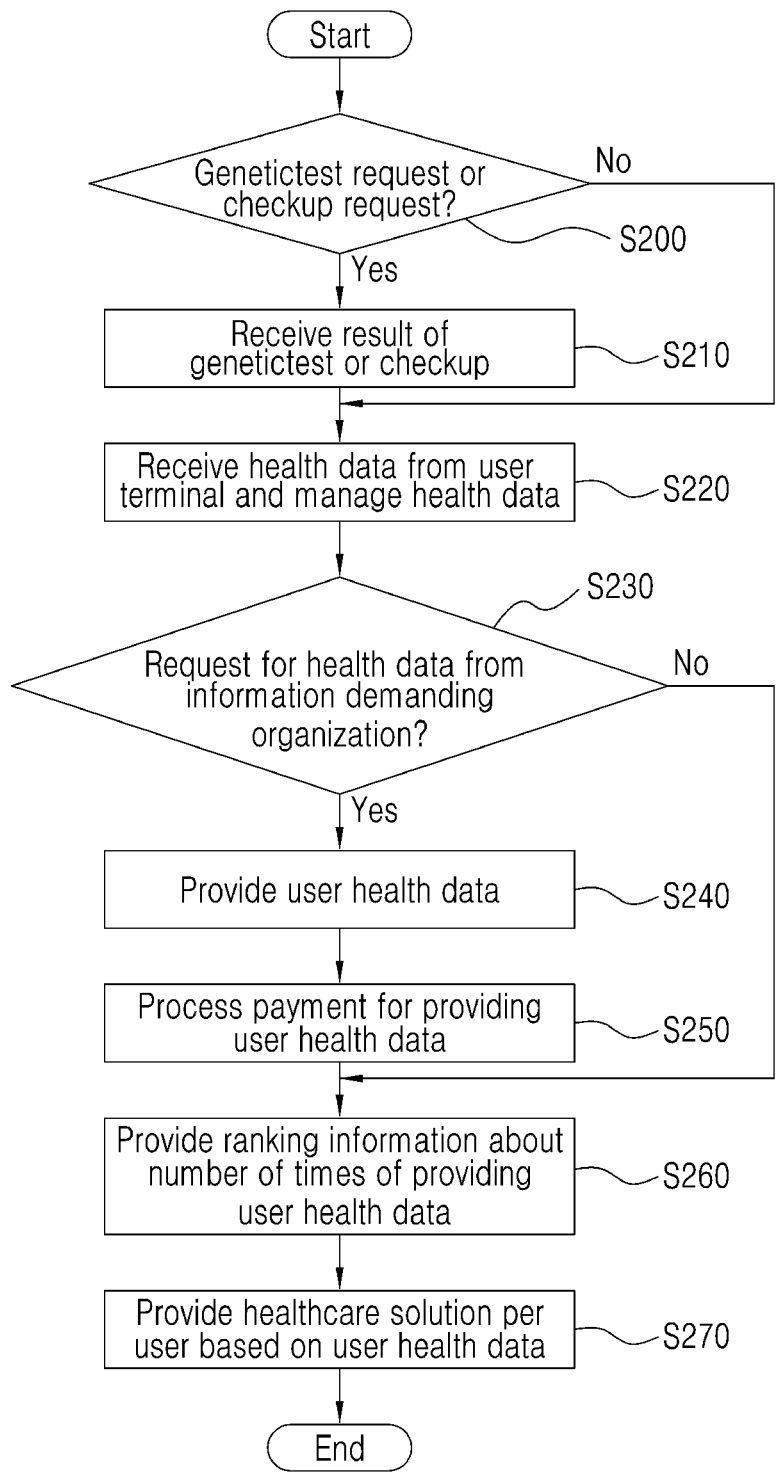
FIG. 2 is a flowchart illustrating a method of driving a health data managing system according to an embodiment of the present invention.

FIG. 2 is a flowchart illustrating a method of driving a health data managing system according to an embodiment of the present invention.

Referring to FIG. 2, in a method of driving a blockchain-based health data managing system, the request receiving unit receives a genetic test request or a health checkup request from the user terminal (S200).

The user may access the genome web portal, which the health data managing system provides, by way of the user terminal to thereby request a genetic testing service and conduct a survey.

The request receiving unit may recommend a test organization or book a test for the user's genetic testing based on the genetic testing service request and the results of the survey.

The results of the genetic test performed in response to the genetic test request are obtained and stored and managed as user health data (S210).

In other words, the information managing unit obtains the results of the genetic test performed in response to the genetic test request and stores and manages the genetic test results as user health data. The information managing unit may obtain the genetic test results from the user terminal or directly from the test organization which was recommended or booked for.

The user terminal may provide user health data including at least one of genetic information, checkups, or prescriptions which have previously been stored.

The information managing unit receives user health data including at least one of genetic information, checkups, or prescriptions from a user terminal, stores and manages the user health data. The information managing unit 100 manages user information and the user health data in a blockchain-based decentralized identity (DID) manner (e.g., MS decentralized identity (DID)).

The decentralized identity (DID) is blockchain-based electronic identity verification technology that stores users' personal information in the users' terminal, i.e., user terminals and, upon authentication, allows only information necessary for authentication to be selected and provided.

The DID, also called a self-sovereign identity, may call in only prior authentication information without the need for login or authentication at each time it is required. Thus, the DID may relieving users of such hassles or inconveniences as photographing, scanning or copying their ID card or entering information whenever required.

The user's gene (genome) data is uploaded once, but medical information, such as checkup results or prescriptions, or social data is continuously uploaded and accrued over time. Thus, it is preferable to steadily upload individuals' health data so that such information or data may have continuity.

The information providing unit, upon receiving a request for user health data from a health data demanding organization (3230), extracts part of the user health data stored and managed and provides the extracted information to the health data demanding organization (S240).

The health data demanding organization may be one of pharmaceutical companies, medical device manufacturers, insurance companies, food/cosmetics companies, research institutes, or schools. Without limitations, however, the health data demanding organization is interpreted to encompass all other kinds or types of business, enterprises, organizations or groups which need users' health-related information.

The request for user health data from the health data demanding organization may include filtering reference information about the health data. For example, the filtering reference information may include filtering references, such as the user's gender and age and whether they suffer from a particular disease. The information providing unit extracts and provides user health data that meets the filtering references included in the user health data request received from the health data demanding organization.

According to an embodiment, while the user's health bigdata is shared, the data owner may be anonymously handled, and the network address of the genome web portal provided by the health data managing system is treated as an encryption identity which is unrelated to the personal information.

Thus, purchases of health data, i.e., the health data demanding organizations, are limited to transparent persons whose identities have been verified by the health data managing system, and all transaction records are perpetually stored in the genome web portal block chains the health data managing system provides.

Thereafter, the payment processing unit receives a cryptocurrency, as a return on providing the user health data, from the health data demanding organization and provide the user, who has provided the user health data, with a cryptocurrency as a reward for providing the user health data (S250).

According to an embodiment, the rewarding step may include receiving the money, which is provided to the genetic test organization or checkup organization, as a cryptocurrency, for the genetic test request or checkup request from the user terminal, The money is transferred in the form of cryptocurrency to the genetic test organization or checkup organization.

According to an embodiment of the present invention, the method may further include the step of counting the number of times in which user health data has been provided in response to requests from the health data demanding organization and providing data providing ranking information, by the ranking information providing unit (S260).

The ranking information providing unit counts the numbers of times in which user health data has been provided to pharmaceutical companies, medical device manufacturers, insurance companies, food/cosmetics companies, research institutes, schools, or other health data demanding organizations and rank them in descending order of the numbers of times. The ranking information is provided to the users who uploaded their health data or to the health data demanding organizations.

According to an embodiment of the present invention, the solution providing unit determines health supplement foods, customized medication, or customized medical organization information, which is necessary to the user, based on artificial intelligence (AI) and the user health data and provides an individual customized health solution (S270).

The health solution is interpreted to encompass all kinds or pieces of information which may contribute to the user's health, such as exercise information or diet information helpful for staying healthy or cosmetics.

Figure 3:
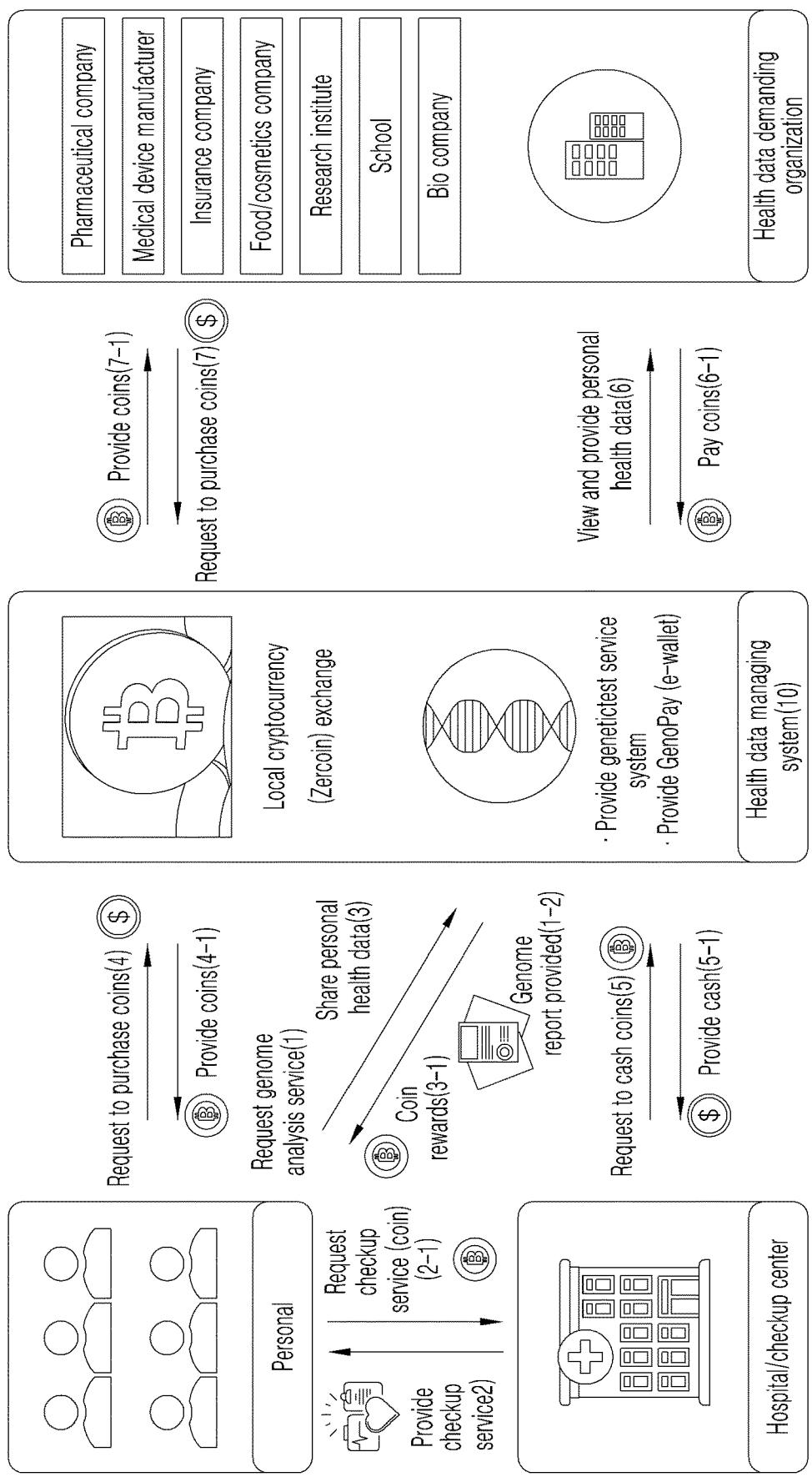
FIGS. 3 and 4 are views illustrating example operations of a health data managing system according to an embodiment of the present invention.
Figure 4:
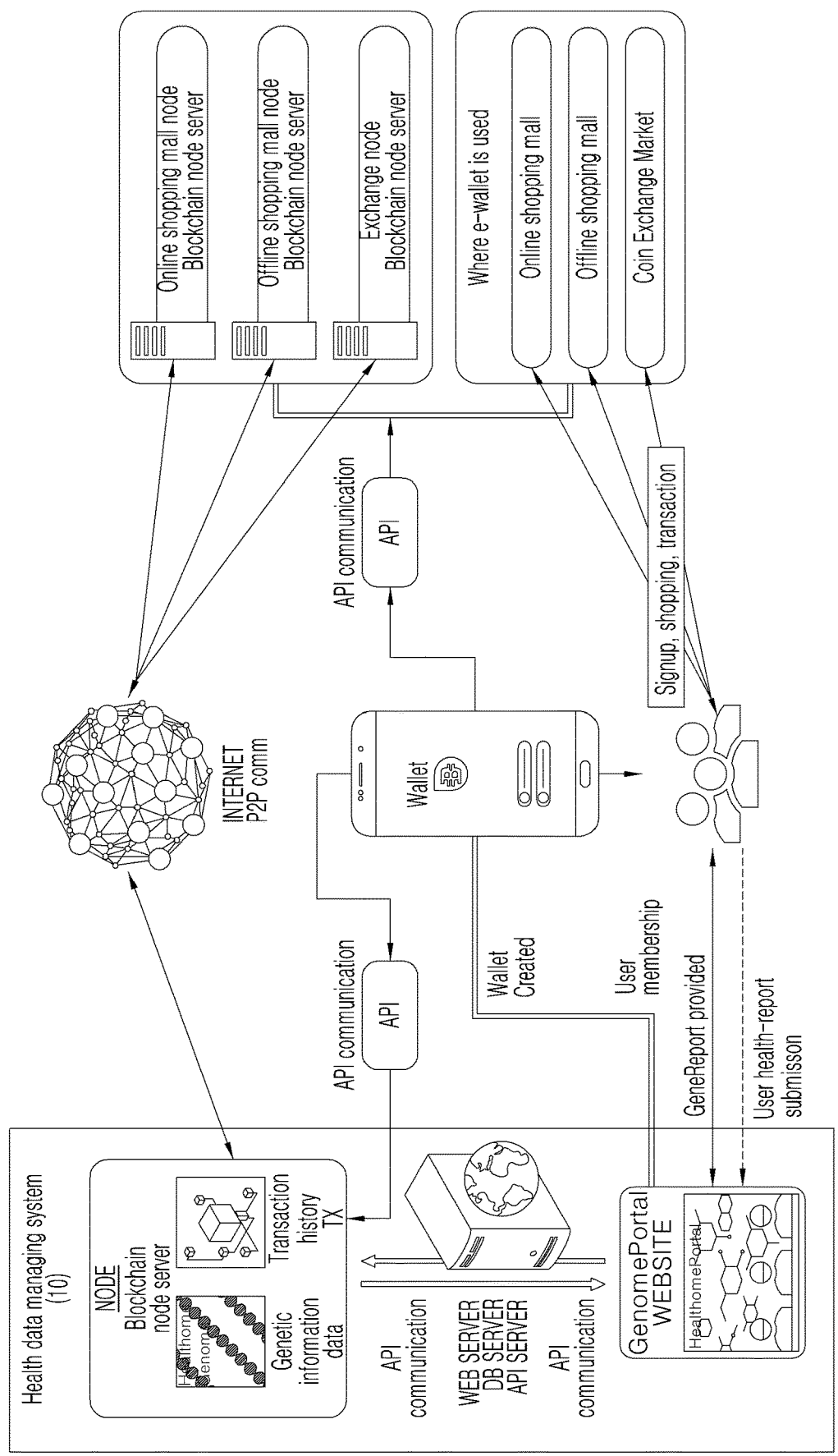

FIGS. 3 and 4 are views illustrating example operations of a health data managing system according to an embodiment of the present invention.

Referring to FIG. 3, a user (e.g., a person) may access the genome web portal, which the health data managing system 10 provides, on her user terminal. The user may access the genome web portal to thereby request a genetic test (genome analysis) or a checkup service and respond to a survey (1).

The survey may include various types of questions or inquires to figure out MBTI, characters, personality, affection, mental health, blood type, and left- or right-brain dominance. However, embodiments of the disclosure are not limited thereto.

The results of a genetic test or health checkup may then be obtained (1-2). In this case, for a genetic test (genome analysis) or health checkup service, the user may visit an affiliated hospital or examination center to receive the genetic test or health checkup.

The user may access the genome web portal, which the health data managing system 10 provides, and applies to share her personal health data (3). Sharing personal health data may mean or include uploading the user's genome information, checkup, or prescription information onto the genome web portal.

The user may receive dedicated coins, e.g., Zerocoins, as a reward for sharing her personal health data (3-1).

According to an embodiment, the user may pay dedicated coins for the genetic test or checkup which the user has received (2-1), and the hospital or checkup center may encash the dedicated coins in a local cryptocurrency exchange operated by the health data managing system 10 (5, 5-1).

The user may purchase dedicated coins in the local cryptocurrency exchange (4, 4-1).

According to an embodiment, the genome web portal provides points, which correspond to 5% of the whole payment, to the customer who paid for the genetic test service. The user receives points as a reward for sharing her own health data. The user may exchange the received points for dedicated coins, that is, Zerocoin, at a local exchange. In this case, Zerocoin is received by the Zerocoin e-wallet in the genome web portal. The e-wallet may automatically be generated when the user signs up in the web portal.

Further, the user may exchange the received Zerocoin with cash at a local virtual currency exchange and obtain additional coins through payment by cash (4, 4-1). Further, the user may use it instead of cash for a checkup service at an affiliated hospital and examination center (2-1). It is preferable to allow cash and Zerocoins to be interchangeably used for payment in the hospital or checkup center.

When the user receives a checkup service using Zerocoins in the hospital/checkup center, payment may be made via a mobile payment app provided from the genome web portal, and coins used for payment may be received and stored in the e-wallet of the hospital/checkup center. As set forth above, the hospital/checkup center may request cashing of their owned Zerocoins in the local exchange in the genome web portal (5, 5-1).

The genome web portal the health data managing system 10 provides a ranking system depending on the number of times in which data has been shared. The genome web portal may recommend a customized health solution to the member who has shared her data via AI, The health solution may include health supplement foods, customized medications, or customized medical organization information.

According to an embodiment, the user may purchase necessary products (e.g., health supplement foods or cosmetics) in a Zerocoin-dedicated shopping mall provided in the genome web portal.

The health data demanding organizations (e.g., pharmaceutical companies, medical device manufacturers, insurance companies, food/cosmetics companies, research institutes, schools, or bio companies) demanding personal health data (medical information, genome information, or social information) may view and purchase the personal health data on the genome web portal (6) and, in this case, Zerocoins may be used to purchase the health data (6-1).

The health data demanding organization may purchase Zerocoins in the self-local cryptocurrency exchange in the genome web portal (7, 7-1).

When the health data demanding organization views or purchases personal health data on the genome web portal, Zerocoins, as a reward, are provided to the user who has uploaded the corresponding health data.

Referring to FIG. 4, according to an embodiment, the health data managing system 10 generates and distributes blockchain a main node NODE The blockchain main node NODE generates cryptocurrency, i.e., Zerocoin.

The blockchain main node NODE may pre-issue a pre-determined amount of Zerocoin among the total amount of Zerocoin to be issued. The pre-issued coins may be used to reward individual users, e.g., customers, for obtaining their health data information.

Coins not issued may be rewarded by mining to node server installers according to a node distribution.

Each user may be assigned an e-wallet while simultaneously signing up in the web portal provided by the health data managing system. The web portal may be implemented to allow the user to simultaneously sign up for the web portal, online shopping malls selling healthy foods, online shopping malls providing genetic information-related additional services, a local exchange where dedicated coins are transacted and cashed, and hospitals or checkup organizations providing genetic test or checkups.

Alternatively, the web portal may also be implemented to be signed up by the user for separately from online shopping malls selling healthy foods, online shopping malls providing genetic information-related additional services, a local exchange where dedicated coins are transacted and cashed, and hospitals or checkup organizations providing genetic test or checkups.

In this case, although the user individually signs up for each web site, an e-wallet may be generated per website simultaneously with the sign-up.

The user may receive dedicated coins as a reward for providing her own health data. The coins received as a reward may be used in associated shopping malls, cashed in the local exchange, or utilized as currency on the e-wallet.

As shown in FIG. 4, the e-wallet may be used in online/offline shopping malls or coin markets. However, the present invention is not limited thereto, and various changes may be made thereto.

According to an embodiment, the health data managing system 10 may perform application programming interface (API) communication, An API is a pre-defined communication rule or a set of such rules to allow other programs to access the functions or data of a particular program.

In particular, use of an open API allows pin-tech companies to access the functions or data of financial companies and use them for developing relevant services or products, and as such, the uses of open APIs are increasing.

The above-described method may be implemented as an application or in the form of program instructions executable through various computer components, which may then be recorded in a computer-readable recording medium. The computer-readable medium may include programming commands, data files, or data structures, alone or in combinations thereof.

The programming commands recorded in the computer-readable medium may be specially designed and configured for the present invention or may be known and available to one of ordinary skill in the computer software industry.

Examples of the computer readable recording medium may include, but is not limited to, magnetic media, such as hard disks, floppy disks or magnetic tapes, optical media, such as CD-ROMs or DVDs, magneto-optical media, such as floptical disks, memories, such as ROMs, RAMs, or flash memories, or other hardware devices specially configured to retain and execute programming commands.

Examples of the programming commands may include, but are not limited to, high-level language codes executable by a computer using, e.g., an interpreter, as well as machine language codes as created by a compiler. The above-described hardware devices may be configured to operate as one or more software modules to perform processing according to the present invention and vice versa.

While the present invention has been shown and described with reference to exemplary embodiments thereof, it will be apparent to those of ordinary skill in the art that various changes in form and detail may be made thereto without departing from the spirit and scope of the present invention as defined by the following claims.

The invention claimed is:

1. A blockchain-based health data managing system, comprising:
an information managing unit configured to receive user health data including at least one of genetic information, checkup information, and prescription information from a user terminal, store the user health data, and manage user information and the user health data in a blockchain-based decentralized identity (DID) manner;
an information providing unit configured to, upon receiving a request for user health data from a health data demanding organization, extract part of the user health data managed by the information providing unit and provide the extracted information; and
a payment processing unit configured to receive a cryptocurrency as a return on providing the user health data from the health data demanding organization and provide a cryptocurrency as a reward for providing the user health data to a user who has provided the user health data, wherein the cryptocurrency calculates the value of 1 coin as a unit of human lifespan, and wherein the unit is hour, second, minute, or day.

2. The blockchain-based health data managing system of claim 1, further comprising a request receiving unit configured to receive a genetic test request or a checkup request from the user terminal, wherein the information managing unit is configured to obtain a genetic test result according to the genetic test request and store and manage the genetic test result as user health data.

3. The blockchain-based health data managing system of claim 2, wherein the payment processing unit is configured to receive a cryptocurrency as a return on the genetic test request or the checkup request from the user terminal received by the request receiving unit.

4. The blockchain-based health data managing system of claim 1, further comprising a ranking information providing unit configured to count the number of times in which the information providing unit provides the user health data in response to the request for the user health data from the health data demanding organization and provide ranking information.

5. The blockchain-based health data managing system of claim 1, further comprising a solution providing unit configured to determine health supplement food, customized medication, or customized medical organization information necessary to the user via artificial intelligence (AI) based on the user health data and provide a personal customized health solution.

6. A method of driving a blockchain-based health data managing system, the method comprising:

a step in which an information managing unit receives user health data including at least one of genetic information, checkup information, and prescription information from a user terminal, stores the user health data, and manages user information and the user health data in a blockchain-based decentralized identity (DID) manner;

a step in which an information providing unit, upon receiving a request for user health data from a health data demanding organization, extracts part of the user health data managed by the information providing unit and provides the extracted information; and a step in which a payment processing unit receives a cryptocurrency as a return on providing the user health data from the health data demanding organization and provides a cryptocurrency as a reward for providing the user health data to a user who has provided the user health data, wherein the cryptocurrency calculates the value of 1 coin as a unit of human lifespan, and wherein the unit is hour, second, minute, or day.

7. The method of claim 6, further comprising a step in which a request receiving unit receives a genetic test request or a checkup request from the user terminal, wherein the managing includes obtaining a genetic test result according to the genetic test request and storing and managing the genetic test result as user health data.

8. The method of claim 7, wherein the providing the reward includes receiving a cryptocurrency as a return on the genetic test request or the checkup request from the user terminal received by the request receiving unit.

9. The method of claim 6, further comprising a step in which a ranking information providing unit counts the number of times in which the information providing unit provides the user health data in response to the request for the user health data from the health data demanding organization and provide ranking information.

10. The method of claim 6, further comprising a step in which a solution providing unit determines health supplement food, customized medication, or customized medical organization information necessary to the user via artificial intelligence (AI) based on the user health data and provide a personal customized health solution.

\* \* \* \* \*